United States Patent [19]

Stapp

[11] 4,099,018
[45] Jul. 4, 1978

[54] METHOD FOR THE OXIDATION OF A CONJUGATED DIOLEFIN

[75] Inventor: Paul R. Stapp, Bartlesville, Okla.

[73] Assignee: Phillips Petroleum Company, Bartlesville, Okla.

[21] Appl. No.: 676,258

[22] Filed: Apr. 12, 1976

[51] Int. Cl.² .............................................. C07C 67/05
[52] U.S. Cl. .................... 560/246; 260/410.6; 260/465.4; 260/465 D; 560/1; 560/112; 560/122; 560/183; 560/230; 252/476
[58] Field of Search .......... 260/476 R, 497 A, 497 R, 260/410.6, 468 R, 465.4, 465 D; 560/246, 1, 112, 122, 183, 230

[56] References Cited

U.S. PATENT DOCUMENTS

| | | | |
|---|---|---|---|
| 2,389,187 | 11/1945 | Drewitt | 260/603 |
| 2,497,408 | 2/1950 | Gresham | 260/497 R |
| 3,274,238 | 9/1966 | Kojer | 260/497 A |
| 3,671,577 | 6/1972 | Ono | 260/497 A |
| 3,742,039 | 6/1973 | Ono | 260/497 A |
| 3,872,163 | 3/1975 | Shimizu | 260/497 A |

FOREIGN PATENT DOCUMENTS

| | | | |
|---|---|---|---|
| 1,138,366 | 1/1969 | United Kingdom | 260/497 A |
| 1,170,222 | 11/1969 | United Kingdom. | |

OTHER PUBLICATIONS

Uemura, Chemical Communications, pp. 1630–1631, (1970).
Crieger, Chem. Abst., 24, pp. 5286–5287 (1930).

*Primary Examiner*—Robert Gerstl
*Assistant Examiner*—Michael Shippen

[57] ABSTRACT

A conjugated diolefin is reacted with at least one compound selected from the group consisting of a carboxylic acid and a carboxylic acid anhydride in the presence of oxygen and a catalyst comprising a lead compound.

10 Claims, No Drawings

METHOD FOR THE OXIDATION OF A CONJUGATED DIOLEFIN

BACKGROUND OF THE INVENTION

The invention relates to a method suitable for the oxidation of a conjugated diolefin. In another aspect the invention relates to a composition useful as a catalyst.

It is desirable to oxidize conjugated diolefins, such as 1,3-butadiene and/or 2-methyl-1,3-butadiene to produce various compounds such as the ethylenically unsaturated esters. A more specific illustration is the oxidation of 1,3-butadiene to produce 1,4-diacetoxy-2-butene. The diacetoxybutene is then easily converted, by processes well known in the art, to other compounds such as tetrahydrofuran or 1,4-butanediol. Although there are various processes and catalysts known which are useful for the oxidation of a conjugated diolefin, most of these processes are relatively expensive to carry out and frequently corrosion of process equipment is a problem. Therefore new processes and catalysts are desirable in an effort to more fully develop the art and improve the overall process.

An object of the present invention is to oxidize a conjugated diolefin.

Another object of the invention is to oxidize a conjugated diolefin more economically than can be done presently.

Another object of the invention is to provide a catalyst useful for the oxidation of conjugated diolefins.

Other objects, advantages and aspects of the present invention will be apparent to those skilled in the art after studying the specification and appended claims.

SUMMARY OF THE INVENTION

In accordance with the invention a conjugated diolefin is reacted with a compound selected from the group consisting of a carboxylic acid and a carboxylic acid anhydride in the presence of oxygen and a catalyst comprising a lead compound.

Further in accordance with the invention a composition useful as a catalyst comprises a lead compound in combination with at least one additional compound selected from the group consisting of an alkali metal salt and a halogenated olefin having a halogen atom in the allylic position.

DETAILED DESCRIPTION OF THE INVENTION

The conjugated diolefins suitable for use in the process of the invention are selected from a wide range of compounds. Generally the conjugated diolefins employed in the process of the instant invention are those having from 4 to 12 carbon atoms per molecule. Suitable conjugated diolefins include acyclic as well as cyclic compounds and further include compounds which have substituents such as a halogen, cyano, or carbalkoxy radical present in the molecule. Presently preferred conjugated diolefins are those containing only carbon and hydrogen because use of such materials produces products finding particular applicability today. For the same reason, the compounds especially preferred for use in the instant invention are 1,3-butadiene and 2-methyl-1,3-butadiene (isoprene) to produce the corresponding 1,4 diacetoxy derivatives. Examples of suitable conjugated diolefins besides 1,3-butadiene and 2-methyl-1,3-butadiene include 2-chloro-1,3-butadiene; 2-ethyl-1,3-butadiene; 2-chloro-3-methyl-1,3-butadiene; 1,3-hexadiene; 1,3-pentadiene; 1,3-octadiene; 1,3-cyclohexadiene; 1,3-cyclooctadiene; 1,3-cyclododecadiene; 2-cyano-1,3-butadiene; and 2-carbethoxy-1,3-butadiene. Mixtures of conjugated olefins are also suitable; however, a mixture of products will result which may be difficult to separate into the individual component products.

The conjugated diolefin is reacted with at least one compound selected from the group consisting of a carboxylic acid and a carboxylic acid anhydride to produce the corresponding diacyloxyalkene. In most instances it is preferred to use a carboxylic acid and the corresponding acid anhydride because the use of the corresponding acid anhydride, in addition to the carboxylic acid, serves to simplify the purification and separation steps by reducing the amount of by-products which contain free hydroxy groups. However, it is within the scope of the invention to use a carboxylic acid alone, a carboxylic acid anhydride alone, a carboxylic acid and a carboxylic acid anhydride of a different carboxylic acid or a carboxylic acid and the corresponding acid anhydride. If the reaction is carried out using a carboxylic acid and a carboxylic acid anhydride of a different carboxylic acid, a mixture of reaction products normally results.

The carboxylic acids and acid anydrides suitable for use in the invention are selected from a large variety of compounds. Generally the acids and acid anhydrides mono- and dicarboxylic acids and acid anhydrides having from about 2 to about 18 carbon atoms per molecule. Such compounds include both aromatic and aliphatic compounds. Furthermore, they can contain halogen or cyano groups or other substituents which are essentially inert to the oxidizing conditions employed for the process of this invention. It is preferred, of course, that the carboxylic compounds employed be normally liquid or at least liquid under the reaction conditions for ease in handling. Acetic acid and acetic anhydride are presently the preferred carboxylic acid and acid anhydride for use according to the process of this invention. Examples of other suitable carboxylic acids include propanoic acid, butanoic acid, pentanoic acid, hexanoic acid, octanoic acid, dodecanoic acid, octadecanoic acid, cyclopentanecarboxylic acid, cyclohexanecarboxylic acid, benzoic acid, chloroacetic acid, cyanoacetic acid, trichloroacetic acid, 2-bromododecanoic acid, 2-ethylhexanoic acid, and the respective acid anhydrides. Mixtures of carboxylic acids and acid anhydrides are also suitable; however, a mixture of reaction products normally results.

The oxidation catalyst employed in accordance with the invention is a compound of lead. As known in the art a wide range of lead compounds can be used to practice the present invention. The valence of lead in lead compounds is generally a +2 or a +4. Also some lead compounds contain lead in both the +2 and +4 valence states, such as $Pb_3O_4$ and $Pb_2O_3$. Suitable lead-containing compounds include those in the form of oxides, carboxylates, nitrates, halides, and the like. Specific examples of suitable lead compounds for use as catalysts in the instant invention include lead (II) acetate, lead (IV) acetate, lead (II) butanoate, lead (II) octanoate, lead (II) carbonate, lead (II) bromide, lead (II) chloride, lead (IV) chloride, lead (II) nitrate, lead (II) oxide, lead (IV) oxide, lead (IV) propanoate, and other lead compounds such as $Pb_3O_4$ and $Pb_2O_3$. Mixtures of lead compounds can be employed if desired. It is also within the scope of this invention to employ lead compounds dispersed in and on an inert support material such as, for example, silica and clays.

It is optional, although presently preferred, to also include as a component of the catalyst system an alkali metal salt such as, for example, a halide, carboxylate or an oxide. The use of such an alkali metal salt generally increases selectively and conversion. Of the alkali metal salts which are employed, the lithium salts are especially preferred for use as the optional cocatalyst component for the process of this invention because of their greater solubility in organic solvents as compared to other alkali metal salts, and as a result of their greater solubility, they are a more effective cocatalyst. When present, the alkali metal salt is employed at a concentration of from about 0.1 to about 2.0 moles per mole of carboxylic acid present as diluent and reactant if used; otherwise, per mole of the carboxylic acid anhydride. However, good results were obtained using a molar ratio ranging from about 0.7 to about 1.5. Examples of alkali metal salts suitable for use in the invention include lithium chloride, lithium bromide, lithium iodide, lithium acetate, lithium benzoate, lithium oxide, lithium octadecanoate, sodium chloride, sodium bromide, sodium acetate, potassium chloride, potassium acetate, potassium benzoate, rubidium chloride, rubidium bromide, rubidium acetate, cesium chloride, cesium acetate, and cesium oxide. Mixtures of the alkali metal compounds may be employed if desired.

Another optional catalyst component which is employed in the instant invention is a halogenated olefin with the halogen atom in the allylic position. In some instances it is desirable to form the halogenated olefin in situ by adding halogen gas to the reactor whereby the halogen reacts with the conjugated diene to produce a halogenated olefin. If a halogenated olefin is added to the reaction, generally a dihalogenated olefin, such as, for example, 1,4-dichloro-2-butene, is used.

Actually, 1,4-dichloro-2-butene is the preferred halogenated olefin adjuvant because good results are obtained with it and it is readily available. Generally the presence of a halogenated olefin gives a small increase in the velocity of the reaction and, if used, they are employed in the amout of from about 0.1 to about 10 moles per mole of lead compound. However, good results were obtained using from about 0.5 to about 5 moles per mole of lead compound.

The catalyst concentration employed for the instant invention is expressed in terms of mole percent lead based on the conjugated diolefin employed. The catalyst is effective over a broad range of catalyst concentrations. Generally, the amount of catalyst employed is in the range of from about 0.1 to about 20 mole percent lead compound although good results were obtained using from about 1 to about 15 mole percent of the lead compound based on the conjugated diolefin charged.

The reaction of the instant invention is an oxidation reaction and as such is carried out in the presence of free oxygen. The amount of oxygen present is not believed to be critical although it is recognized that an undesirably slow reaction will result if the concentration of oxygen is very low. Essentially pure oxygen can be employed as well as mixtures of oxygen with inert gases, or air can be employed as a source of free oxygen for the instant reaction. It is recognized that explosive conditions could be obtained if the amount of oxygen added to the reaction system is not under control. The reaction of this invention, as is true with many oxidation reactions, appears to be highly exothermic and this too dictates caution in adding oxygen to the system. Because of these considerations, it is desirable to add the oxygen incrementally or continuously during the reaction to avoid the explosive range of oxygen concentration and to allow better control of the temperature of the reaction. A reaction vessel with efficient mixing means is also desirable to avoid buildup of dangerous concentrations of free oxygen.

The temperature at which the reaction of this invention is carried out is selected over a relatively wide temperature range. Generally a temperature range of from about 30° to about 200° C is employed; however, temperatures ranging from about 100° to about 150° C were used with good success.

Similarly, the oxygen pressure reaction at which the reaction is carried out can be selected over a relatively wide range. Generally the oxygen pressure ranges from about 0.1 to about 1000 psig of oxygen above autogenous pressure of the reactants in the absence of oxygen at the temperature employed; however, good results were obtained employing a range from about 5 to about 200 psig of oxygen above autogenous pressures at the temperature employed.

The reaction time generally depends on the temperature, catalyst activity, the reactants, and the oxygen pressure employed. The reaction time is usually based on the desired conversion of the starting diolefin reactant. The reaction time does not appear to be a particularly significant parameter of the reaction and in some cases a product can probably be produced at very low yields using a reaction time as short as a second; however, much longer reaction times are normally used ranging from about 1 to about 24 hours. Good results were obtained employing a reaction time ranging from about 4 to about 16 hours.

As described above, the reaction of the instant invention is carried out in the presence of a carboxylic acid and/or acid anhydride which provides the acyl moiety of the final product. In most instances, as previously described, it is desirable to employ as part of the reaction mixture the corresponding carboxylic anhydride (in addition to the carboxylic acid) as an optional but preferred component because the carboxylic acid anhydride serves to simplify the purification and separation steps by reducing the amount of by-products which contain free hydroxy groups. When both a carboxylic acid and the corresponding acid anhydride are used, it is desirable to use at least an amount of the acid anhydride equal to the amount of conjugated diolefin on a molar basis because for each mole of the diacyloxyalkene produced, one mole of water is also produced.

The process of the instant invention can be carried out in a batch or a continuous fashion.

Reaction mixtures obtained according to the process of this invention are generally vented to remove any unreacted oxygen and conjugated diolefin and then distilled to remove the carboxylic acid present. The product remaining is usually distilled to recover one or more fractions containing the diacyloxy olefins. The catalyst is usually recovered from the distillation residue and recycled to the reaction zone.

The isomeric materials which are recovered from the product mixture include in many instances an amount of 1,2-isomer which can be recycled to the reaction zone and thereby converted to the more desirable 1,4-diacyloxy olefin.

The above-mentioned 1,4-diacyloxy olefins have utility as intermediates for the preparation of the corresponding saturated diols. For example, as previously noted, it is known to prepare tetrahydrofuran or 1,4-butanediol starting with a conjugated diolefin and proceeding through 1,4-diacyloxy butene.

lation of the residue and analyzed by GLC. In run 4 only the residue was analyzed by GLC.

TABLE I

| Run No. | Lithium halide | 1,4-Dihalo--2-butene | Butadiene mmole | Time, hrs. | Temp. C | Diacetoxybutenes | |
|---|---|---|---|---|---|---|---|
| | | | | | | mmol | % Yield[a] |
| 1 | Cl | Cl | 194.4 | 4 | 140 | 46.2[b] | 24 |
| 2 | Cl | Cl | 194.4 | 5.75 | 100 | 18.8[c] | 10 |
| 3 | Br | Br | 201.9 | 5 | 140 | 55.2 | 27 |
| 4 | Cl | Cl | 203.7 | 6 | 140 | 98.0 | 48 |

[a] Yield of diacetoxybutenes based on butadiene charged.
[b] Also found were 1-acetoxy-2-hydroxy-3-butene (about 13.6 mmol); 1,2-dichloro-2-butene (4.2 mmole); 1-acetoxy-4-chloro-2-butene (16.2 mmol) and a trace amount of 1-acetoxy-2-chloro-3-butene.
[c] Also found were 1-acetoxy-2-hydroxy-3-butene (about 15.8 mmol); 1,2-dichloro-2-butene (12.2 mmol); 2-acetoxy-1-hydroxy-3-butene (3.4 mmol) and a trace amount of 1-acetoxy-2-chloro-3-butene.

EXAMPLE I

A 250 ml glass pressure reactor, Fisher-Porter aerosol compatibility bottle, equipped with a magnetic stirrer was charged with 49.2 grams (100 mmol) of lead tetraacetate (90%) and 100 ml of acetic acid. The bottle was chilled and evacuated and then charged with 10.7 grams (198.1 mmol) of butadiene from the vapor phase. The reaction mixture was stirred at room temperature (about 26° C) for 16 hours. At the end of this reaction period, the unreacted butadiene was distilled into a cold trap and 2.2 grams were recovered. The reaction mixture was filtered and the solid was washed with acetic acid. The filtrate was distilled through an 18 inch Vigreaux column and additional butadiene was observed to flash off during the early stages of the distillation period. Following distillation of the acetic acid there was no residue remaining, indicating that the desired oxidation of butadiene had not taken place.

The above run is a control run in that oxygen was not present during the reaction. As can be seen from the results, essentially no oxidation of the butadiene took place in the absence of added oxygen under the conditions employed.

EXAMPLE II

A series of four runs was conducted in the same apparatus as that employed in Example I. Each run was charged with 21.5 mmol of dihalobutene, 75 mmol of lithium halide, 25 mmol of lead tetraacetate, 50 ml of acetic acid and 25 ml (265 mmol) of acetic anhydride. In each run, the reactor was chilled and evacuated and about 200 mmol of butadiene (exact amount shown in the table below) was charged in the vapor phase. The reactor was pressured to 30 psig with oxygen and placed in an oil bath and heated to the designated temperature. About 30 minutes of heating time was required to reach the temperature shown. During each reaction, oxygen was added intermittently to maintain the pressure at 110—125 psig. At the end of each run the reactor was vented and the solid material separated from the liquid phase by filtration. The filtrate was fractionally distilled under reduced pressure to remove the acetic acid. The residue from the stripping of the acetic acid was dissolved in ether, water washed, neutralized ($Na_2CO_3$), dried over $MgSO_4$, ether evaporated and then except for run 4 fractionally distilled under reduced pressure. The fractions were analyzed by gas-liquid phase chromatography (GLC). In run 1 six overhead fractions were obtained on distillation of the residue and analyzed by GLC. In runs 2 and 3 five and one overhead fractions respectively were obtained on distil-

EXAMPLE III

Another run was conducted according to the process of the instant invention using the same apparatus as employed in Examples I and II. The reactor was charged with 4.6 grams (21.5 mmol) of 1,4-dibromo-2-butene, 6.5 grams (75 mmol) of lithium bromide, 9.8 grams (30 mmol) of lead (II) acetate, 50 ml of acetic acid, 25 ml (265 mmol) of acetic anhydride and 10 grams (185.2 mmol) of butadiene charged in the vapor phase. The reactor was placed in an oil bath, pressured to 30 psig with oxygen and heated to 140° C. During the reaction, the reactor was pressured intermittently to 120 psig with oxygen as in the previous runs of Example II. The reaction was conducted for 6 hours at 140° C after the reaction temperature was reached which required about 1 hour. At the end of the reaction, the reactor was vented and the reaction mixture filtered to recover the filtrate. The filtrate was distilled to remove the acetic acid. The distillation residue was dissolved in ether, washed with sodium carbonate solution, dried over magnesium sulfate, filtered, and the ether stripped off on a rotary evaporator. The residue weighed 19.4 grams and was analyzed by gas-liquid phase chromatography. The analysis showed that 14.3 mmol of 1,2-diacetoxy-3-butene and 89.5 mmol of 1,4-diacetoxy-2-butene had been obtained in the reaction. This represents a total yield of 56 percent of the diacetoxybutenes based on the butadiene charged. This run demonstrates that lead (II) salts are suitable catalysts for the instant invention.

EXAMPLE IV

Another run was carried out according to the process of this invention using the same apparatus as employed in the previous examples. In this run, the reactor was charged with 11.1 grams (25 mmol) of lead tetraacetate, 50 ml of acetic acid, 25 ml (265 mmol) of acetic anhydride, and 10 grams (185.2 mmol) of butadiene charged in the vapor phase. The reactor was pressured to 30 psig with oxygen, placed in an oil bath, and heated to 140° C. As in previous runs, the reactor was pressured intermittently to 120 psig with oxygen. The reaction time for this run was 5.7 hours with about one additional hour being required to reach the 140° C temperature. At the end of the reaction, the reactor was vented and the acetic acid distilled out of the mixture at reduced pressure. The reaction residue was mixed with 200 ml of ether, filtered and the recovered solid washed with ether. The filtrate and the ether washings were washed with water, neutralized with sodium carbonate, dried over magnesium sulfate, filtered, and the ether removed on a rotary evaporator. The recovered residue weighed 18.0 grams. This material was analyzed by gas-liquid phase chromatography as before and it was found that 42.6 mmol of 1,2-diacetoxy-3-butene and 20.6 mmol of 1,4-diacetoxy-2-butene had been obtained in this reaction. This represents a yield of 34 percent of the diacetoxybutenes based on the butadiene charged. In this run, it was noted that the residue obtained after stripping off the ether contained about 4 grams of an unknown material.

The above result demonstrates that the instant invention can be achieved by the lead catalysts alone, i.e., in the absence of added alkali metal salt and dihalobutene. However, the result indicates that better yields of the desired diacetoxybutenes are obtained when these additional materials are present as part of the catalyst system.

What is claimed is:

1. A method for the production of a diacyloxyalkene comprising:
contacting a mixture comprising a conjugated diolefin, oxygen and at least one compound selected from the group consisting of a carboxylic acid and a carboxylic acid anhydride using a catalyst consisting essentially of a lead compound and an alkali metal salt wherein the number of carbon atoms in the conjugated diolefin ranges from about 4 to about 12, the conjugated diene is selected from unsubstituted compounds and substituted compounds wherein the substituents are selected from the group consisting of halogen, cyano and carbalkoxy radicals, the carboxylic acid and carboxylic acid anhydride are selected from the group consisting of mono- and dicarboxylic aliphatic and aromatic acids and acid anhydrides having from about 2 to about 18 carbon atoms per molecule, and the lead compound is selected from the group consisting of oxides, carboxylates, nitrates, halides and mixtures thereof.

2. The method of claim 1 wherein the reaction is carried out in the presence of a carboxylic acid and the carboxylic acid anhydride corresponding to the carboxylic acid.

3. The method of claim 1 wherein the conjugated diolefin is selected from the group consisting of 1,3-butadiene, 2-methyl-1,3-butadiene, 2-chloro-1,3-butadiene, 2,-ethyl-1,3-butadiene, 2-chloro-3-methyl-1,3-butadiene, 1,3-hexadiene, 1,3-pentadiene, 1,3-octadiene, 1,3-cyclohexadiene, 1,3-cyclooctadiene, 1,3-cyclododecadiene; 2-cyano-1,3-butadiene, and 2-carbethoxy-1,3-butadiene;
the carboxylic acid and the carboxylic acid anhydride are selected from the group consisting of acetic acid, propanoic acid, butanoic acid, pentanoic acid, hexanoic acid, octanoic acid, dodecanoic acid, octadecanoic acid, cyclopentane-carboxylic acid, cyclohexanecarboxylic acid, benzoic acid, chloroacetic acid, cyanoacetic acid, trichloroacetic acid, 2-bromododecanoic acid, 2-ethylhexanoic acid and the acid anhydrides thereof; and
the lead compound is selected from the group consisting of lead (II) acetate, lead (IV) acetate, lead (II) butanoate, lead (II) octanoate, lead (II) carbonate, lead (II) bromide, lead (II) chloride, lead (IV) chloride, lead (II) nitrate, lead (II) oxide, lead (IV) oxide, lead (IV) propanoate, $Pb_3O_4$, $Pb_2O_3$, and mixtures thereof.

4. The method of claim 1 wherein the amount of catalyst employed ranges from about 0.1 to about 20 mole percent lead compound based upon the amount of conjugated diolefin.

5. The method of claim 1 wherein the alkali metal salt is selected from the group consisting of lithium chloride, lithium bromide, lithium iodide, lithium acetate, lithium benzoate, lithium oxide, lithium octadecanoate, sodium chloride, sodium bromide, sodium acetate, potassium chloride, potassium acetate, potassium benzoate, rubidium chloride, rubidium bromide, rubidium acetate, cesium chloride, cesium acetate, cesium oxide, and mixtures thereof.

6. The method of claim 1 wherein the reaction is carried out in the presence of a halogenated olefin having a halogen atom in the allylic position.

7. The method of claim 1 wherein the reaction is carried out in the presence of a carboxylic acid and a carboxylic acid anhydride corresponding to the carboxylic acid, an alkali metal salt, and a halogenated olefin having the halogen atom in the allylic position,
wherein the amount of the carboxylic acid anhydride is at least equal to the amount of conjugated diolefin on a molar basis, the amount of the alkali metal salt ranges from about 0.1 to about 2 moles per mole of conjugated diolefin, the amount of the halogenated olefin ranges from about 0.1 to about 10 moles per mole of lead compound, the amount of catalyst employed ranges from about 0.1 to about 20 mole percent lead compound based upon the amount of conjugated diolefin, the reaction temperature ranges from about 30° C to about 200° C, the reaction pressure ranges from about 0.1 to about 1000 psig of oxygen above autogenous pressure, and the reaction time ranges from about 1 to about 24 hours.

8. The method of claim 7 wherein the amount of alkali metal salt ranges from about 0.7 to about 1.5 moles per mole of conjugated diolefin, the amount of the halogenated olefin ranges from about 0.5 to 5 moles per mole of lead compound, the amount of catalyst employed ranges from about 1 to about 15 mole percent lead compound based upon the amount of conjugated diolefin, the reaction temperature ranges from about 100° C to about 150° C, the reaction pressure ranges from about 5 to about 200 psig of oxygen above autogenous pressure, and the reaction time ranges from about 4 to about 16 hours.

9. The method of claim 7 wherein the conjugated diolefin is selected from the group of 1,3-butadiene and 2-methyl-1,3-butadiene, the carboxylic acid is acetic acid, the alkali metal salt is a lithium halide, and the halogenated olefin is 1,4-dichloro-2-butene.

10. The method of claim 9 wherein the lead compound is selected from the group of lead tetraacetate and lead (II) acetate and the lithium halide is selected from the group consisting of lithium bromide and lithium chloride.

* * * * *